United States Patent
Kato et al.

(10) Patent No.: US 9,055,739 B2
(45) Date of Patent: Jun. 16, 2015

(54) COMPOSITIONS FOR CRYOPRESERVATION OF CELLS

(75) Inventors: Yoichi Kato, Echizen (JP); Masahiro Sasaki, Fukui (JP); Hideyuki Yamada, Fukui (JP)

(73) Assignee: SEIREN KABUSHIKI KAISHA, Fukui-Ken (JP)

( * ) Notice: Subject to any disclaimer, the term of this patent is extended or adjusted under 35 U.S.C. 154(b) by 1884 days.

(21) Appl. No.: 11/663,539

(22) PCT Filed: Sep. 26, 2005

(86) PCT No.: PCT/JP2005/017577
§ 371 (c)(1),
(2), (4) Date: Mar. 22, 2007

(87) PCT Pub. No.: WO2006/033429
PCT Pub. Date: Mar. 30, 2006

(65) Prior Publication Data
US 2009/0197331 A1 Aug. 6, 2009

(30) Foreign Application Priority Data
Sep. 24, 2004 (JP) ................................. 2004-276951

(51) Int. Cl.
*C12N 5/00* (2006.01)
*A01N 1/00* (2006.01)
*A01N 1/02* (2006.01)
*C07K 14/435* (2006.01)
*C12N 1/04* (2006.01)

(52) U.S. Cl.
CPC ............... *A01N 1/02* (2013.01); *A01N 1/0221* (2013.01); *C07K 14/43586* (2013.01); *C12N 1/04* (2013.01)

(58) Field of Classification Search
IPC .............. A01N 1/02,1/0221; C12N 1/04; C07K 14/43586
See application file for complete search history.

(56) References Cited

U.S. PATENT DOCUMENTS 7,943,293 B2 * 5/2011 Cecchi ........................... 435/1.3

FOREIGN PATENT DOCUMENTS

| EP | 1 321 473 | 6/2003 |
| EP | 1 347 040 | 9/2003 |
| JP | 2002-101869 | 4/2002 |
| SU | 1 189 448 | 11/1985 |

OTHER PUBLICATIONS

Gomori, 1955. Preparation of Buffers for Use in Enzyme Studies. Methods in Enzymology, vol. 1, pp. 138-146.*
Wikipedia. 2010. http://en.wikipedia.org/wiki/Tris, pp. 1-3, Modified Apr. 20, 2010, Printed Jul. 3, 2010.*
Zhang et al. 2004. Immobilization of L-asparaginase on the microparticles of the natural silk sericin protein and its characters. Biomaterials, vol. 25, pp. 3751-3759.*
Hubálek. Z. 2003. Protectants used in the cryopreservation of microorganisms. Cryobiology, vol. 46, pp. 205-229.*
Sasaki et al. 2005. Biotechnology and Applied. Biochemistry, vol. 42, pp. 183-188, Rapidly published on Jun. 8, 2005, doi: 10.1042/BA20050019.*
Mohan. 2003. Calbiochem a guide for the preparation and use of buffers in biological systems. Copyright © 2003 EMD Biosciences, Inc., An Affiliate of Merck KGaA, Darmstadt, Germany. All Rights Reserved, 37 Pages.*
Jain et al. 2009. Effect of trehalose on protein structure. Protein Science, vol. 18, No. 1, pp. 24-36 or 1-17).*
T. Toyosawa et al., "Development of Novel Serum-Free Cell Cryopreservative Using Silk Protein Sericin", The Society of Chemical Engineers, p. EP03, 2004 (with English translation).
S. Kono et al., "Cryopreservation of *Eisenia bicyclis* (Laminariales, Phaeophyta) in Liquid Nitrogen", Journal of Marine Biotechnology, vol. 6, pp. 220-223, 1998.
Shizuoka-ken Nousei-bu Nurinsuisan Kankei Shikenkenkyu Seikajoho (Working Papers in Agriculture, Forestry and Fisheries field by Agricultural Policy Planning Division of Shizuoka-Pref. in Japan), pp. 80-81, 1998 (with English translation).
International Search Report issued Aug. 31, 2007 in the International (PCT) Application of which the present application is the U.S. National Stage.
K. Tsujimoto et al., "Cryoprotective Effect of the Serine-Rich Repetitive Sequence in Silk Protein Sericin", Journal of Biochemistry, vol. 129, No. 6, pp. 979-986, Jun. 6, 2001.
J. Kruuv et al., "Protective Effects of Amino Acids Against Freeze-Thaw Damage in Mammalian Cells", Cryobiology, vol. 29, No. 2, pp. 291-295, 1992.
Y. Zhang et al., "Applications of Natural Silk Protein Sericin in Biomaterials", Biotechnology Advances, vol. 20, No. 2, pp. 91-100, May 2, 2002.
S. Terada et al.,"Sericin, A Protein Derived from Silk Worms, Accelerates the Proliferation of Several Mammalian Cells Lines Including a Hybridoma", Cytotechnology, vol. 40, Nos. 1-3, pp. 3-12, Nov. 1, 2002.

* cited by examiner

*Primary Examiner* — Jon P Weber
*Assistant Examiner* — Kailash C Srivastava
(74) *Attorney, Agent, or Firm* — Wenderoth, Lind & Ponack, L.L.P.

(57) ABSTRACT

A composition for the cryopreservation of cells according to the present invention at least comprises sericin and one or more components selected from the group consisting of amino acids and saccharides. Further, a method for the cryopreservation of cells according to the present invention comprises the steps of placing target cells in the abovementioned composition for the cryopreservation of cells and cryopreserving them. According to the composition for the cryopreservation of cells of the present invention, cells can be cryopreserved over a long period of time without the use of serum and components derived from serum.

8 Claims, No Drawings

COMPOSITIONS FOR CRYOPRESERVATION OF CELLS

This application is a U.S. national stage of International Application No. PCT/JP2005/017577 filed Sep. 26, 2005.

CROSS-REFERENCE TO RELATED APPLICATIONS

This application is based upon and claims the benefit of priority from the prior Japanese Patent Application No. 2004-276951 (filed on Sep. 24, 2004), the entire contents of which are incorporated herein by reference.

BACKGROUND OF THE INVENTION

1. Field of the Invention

The present invention relates to a composition for the cryopreservation of cells with which an excellent survival rate of cells can be obtained.

2. Background Technology

Cryopreservation of cultured cells has been carried out for the purpose of preventing the degeneration of the cells by subculturing, preventing the contamination with unwanted bacteria during subculturing, and solving troubles in the maintenance of subcultures. For example, in the case of animal cells, conventionally, a preservation method for animal cells generally uses cryopreservation technology, in which cells are suspended in a culture solution containing 5-15% dimethyl sulfoxide (DMSO) or glycerin or bovine serum, the resulting suspension is sealed into tubes or ampoules for freezing and the sealed products are cooled rapidly at a rate of about $-1°$ C./min using a programmed freezer and ultimately stored in liquid nitrogen ($-196°$ C.).

However, when a culture solution is used for cryopreservation, the survival rate of frozen cells decreases so that it often takes time to grow the cells to a target number when they are thawed. On the other hand, when serum is used for cryopreservation, the cost for preservation increases in the case where various kinds of cell strains are frozen on a large scale since serum is quite expensive. Further, serum largely contains components which are primarily unnecessary for cell preservation, such as various kinds of cytokines, growth stimulating factors, hormones and ions, which likely deteriorates characteristics of preserved cells. Further, in the case where serum is used, or even where albumin purified from serum or plasma is used, problems such as the risk of viral infection still remain.

Furthermore, in the case where a programmed freezer is used, the procedure for cell freezing itself inevitably becomes complicated and the survival rate of the frozen cells problematically decreases as time lapses.

As a cryopreservation fluid with which the use of a programmed freezer is not necessary, for example, Japanese Patent Laid-open Publication No. H6-46840 (No. 1994-46840) has proposed a cryopreservation fluid with which the use of a programmed freezer is not necessary and direct transfer from an ice bath to an atmosphere at a temperature of $-80°$ C. is possible. However, this cryopreservation fluid contains serum components.

Accordingly, a cryopreservation fluid for the preservation of cells with which the use of a programmed freezer is not necessary, and direct transfer from an ice bath to a freezer at $-80°$ C. is possible and cells can be stored frozen over a long period of time without the need for a culture solution, serum, or components derived from serum has been desired.

Conventionally, amino acids, proteins, saccharides, alcohols, and the like are known as components to be used for a cryopreservation fluid for cells. For example, Shinozaki, K. et al.: FEBS Lett., 461(3), 205 (1999) and Takagi, H. et al.: Appl Environ Microbiol, 69(11), 6527 (2003) have reported that an amino acid, proline, has a cryoprotective effect. Further, Japanese Patent Laid-open Publication No. 2002-233356 has disclosed a cryopreservation fluid for cells with the use of saccharides (particularly glucose).

However, as far as the present inventors are aware, the cryoprotective effect of these components alone has not been sufficient as compared to serum components.

On the other hand, a silk protein, sericin, has been confirmed to have a cryoprotective effect on cells in Japanese Patent Laid-open Publication No. 2002-101869.

SUMMARY OF THE INVENTION

The present inventors recently found that the use of a silk protein, sericin, and amino acids and/or saccharides in combination exhibited a cryoprotective effect on cells as excellent as the use of components derived from serum, without the use of components derived from serum. This effect became more marked with the use of specifically selected sericin, and amino acids and/or saccharides in a specific amount. The present invention is based on these findings.

Accordingly, an objective of the present invention is to provide a cryopreservation fluid for cells with which cells can be cryopreserved over a long period of time without the use of serum and components derived from serum.

A composition for the cryopreservation of cells according to the present invention at least comprises sericin and one or more components selected from the group consisting of amino acids and saccharides.

A method for the cryopreservation of cells comprises the steps of placing target cells in the abovementioned composition for the cryopreservation of cells and cryopreserving them.

A composition for the cryopreservation of cells according to the present invention demonstrates an excellent cryoprotective effect as compared to that with the use of sericin alone and also demonstrates an equivalent or better cryoprotective effect as compared to that with the use of components derived from serum. Further, since the composition for the cryopreservation of cells according to the present invention does not contain serum or components derived from serum, there is little possibility for preserved cells to change their characteristics and there is very little risk of contamination with unknown viruses. Since the composition of the present invention has a distinct composition, it is highly safe and maintains its qualitative stability, which is advantageous for its stable supply. Furthermore, with the use of the composition according to the present invention, cells packed into freezing tubes or ampoules can be frozen directly in a freezer at $-80°$ C. without using a programmed freezer, which simplifies the freezing process as compared to that with the use of a conventional cryopreservation fluid for cells. Further, with the use of the composition according to the present invention, cells of interest can be cryopreserved over a long period of time and a high survival rate of the cells can be attained after the cryopreservation. As a result, the time required to grow the cells to a target number can be shortened.

DETAILED DESCRIPTION OF THE INVENTION

Composition for the Cryopreservation of Cells

As described above, the composition for the cryopreservation of cells according to the present invention at least comprises sericin and one or more components selected from the group consisting of amino acids and saccharides. Therefore, the composition according to the present invention can further contain other cryoprotective components (i.e., cryoprotectants) for cells, buffers, and other optional components as long as it contains the abovementioned components. The composition for the cryopreservation of cells according to the present invention is generally used as a cryopreservation fluid in an aqueous solution by adding water. Accordingly, the composition for the cryopreservation of cells herein includes that in a solid state as well as that in a liquid state.

The term "cryopreservation of cells" means to freeze and preserve cells for the purpose of maintaining the cells over a long period of time without subculturing, in which a method for freezing and preserving are not particularly limited. Accordingly, for example, it includes the case where cells are placed directly into a freezer and then frozen and preserved without using a programmed freezer, as well as the case where cells are frozen and preserved using a programmed freezer.

In the present invention, "cells" are not particularly limited as long as the cells can be subjected to cryopreservation. They can be microorganisms, bacteria, animal cells, or plant cells. In the present invention, the "cells" are preferably animal cells. Animals herein include mammals including humans, fish, birds, insects, and the like. The "animal cells" in the present invention can be any type of cells including cells lineaged as cultured cells, non-lineaged normal cells obtained from biological tissues, transformed cells obtained using genetic engineering technology, and the like.

Sericin

In the present invention, sericin can be either derived from nature or artificially synthesized using ordinary chemical and/or genetic engineering techniques. Accordingly, for example, sericin produced by domestic silkworms or wild silkworms can be used. Preferably, sericin is highly purified and substantially contains no impurities.

In the present invention, the term "sericin" includes sericin and its hydrolysates. The hydrolysates of sericin herein can be obtained by hydrolyzing unhydrolyzed sericin by an ordinary method, for example, using alkalies, enzymes, and the like.

In the present invention, sericin can be obtained by the extraction from cocoons, raw silk, and the like using an ordinary extraction method. More specifically, for example, sericin can be obtained by a partial hydrolysis extraction method with hot water, an acid, an alkali, or an enzyme using cocoons, raw silk, or silk goods as a raw material. If necessary, sericin thus obtained is purified to high purity (for example, at 13% or more as the total nitrogen content of solid sericin) and prepared in a solid form such as powder by the method described in Japanese Patent No. 3011759 and the like. In the present invention, this sericin in a solid form can be combined into the composition for the cryopreservation of cells as it is; however, if necessary, sericin in a solid form can be dissolved or suspended in water or a buffer solution to make it into a solution form and then combined into the composition for the cryopreservation of cells.

In the present invention, the average molecular weight of sericin is not particularly limited; however, it ranges preferably 3,000-300,000, more preferably 5,000-100,000, and most preferably 10,000-50,000. When the average molecular weight of sericin is less than 300,000, gelation of an aqueous solution, which occurs at a concentration of about 0.5% by weight, can be arrested, which prevents restriction in the form of use. Further, an average molecular weight of sericin of 3,000 or more is advantageous to exhibit a cellular cryoprotective effect.

In the present invention, the sericin content in the composition for the cryopreservation of cells is not particularly limited; however, the final concentration of sericin is preferably 0.01-10.0% by weight, more preferably 0.1-1% by weight. A final sericin concentration of 0.01% or more by weight is advantageous to exhibit a sufficient cryoprotective effect, and a final concentration of less than 10.0% by weight is advantageous to suppress an increase in cost for preservation.

The expression that the final concentration of sericin in the composition for the cryopreservation of cells is 0.01-10.0% by weight means that the sericin concentration of a preservation fluid which is actually prepared for the use in cryotreatment of cells is 0.01-10.0% by weight. This also applies in the case of amino acids and saccharides.

Amino Acids

In the present invention, amino acids include optical isomers, namely both D-isomers and L-isomers. Further, the term amino acid as used herein includes 20 α-amino acids which construct natural proteins, as well as other α-amino acids, β-, γ-, and δ-amino acids, and unnatural amino acids. Accordingly, for example, the amino acid can be one or more selected from the group consisting of alanine, valine, leucine, isoleucine, proline, phenylalanine, tryptophan, methionine, glycine, serine, threonine, cysteine, glutamine, asparagine, tyrosine, lysine, arginine, aspartic acid, and glutamic acid. Preferably, the amino acid can be one or more selected from the group consisting of proline, glutamine, serine, threonine, glycine, and alanine; more preferably, the amino acid is one or more selected from the group consisting of proline and glutamine.

Further, in the present invention, the term amino acid includes amino acids themselves as well as amino acid derivatives. Examples of the amino acid derivatives include amino acid salts and amino acid solvates. Examples of the amino acid salts include alkaline metal salts or alkaline earth metal salts such as sodium salts, potassium salts, and calcium salts; halogen acid salts such as hydrofluoric acid salts, hydrochloric acid salts, hydrobromic acid salts, and hydroiodic acid salts; inorganic acid salts such as nitrate salts, perchlorate salts, sulfate salts, and phosphate salts; and organic acid salts such as fumarate salts, succinate salts, citrate salts, oxalate salts, maleate salts, acetate salts, lactate salts, and ascorbate salts. Examples of the amino acid solvates include hydrates, alcoholates (for example, methanolates, ethanolates), and etherates (for example, diethyl etherates).

In the present invention, the amino acid content in the composition for the cryopreservation of cells is not particularly limited; however, the final amino acid concentration is preferably 0.01-10.0% by weight, more preferably 0.1-1.0% by weight. A final amino acid concentration within the abovementioned range is advantageous to exhibit a sufficient cryoprotective effect.

Saccharides

In the present invention, the term saccharide also includes oligosaccharides such as monosaccharides and disaccharides, polysaccharides, and the like. The saccharide, for example, can be one or more selected from the group consisting of glucose, xylose, arabinose, fructose, galactose, mannose, mannitol, sorbitol, xylitol, myo-inositol, trehalose, sucrose, lactose, maltose, cellobiose, lactitol, maltitol, methyl cellulose, carboxymethyl cellulose, dextran, glycogen, amylose, amylopectin, inulin, sodium alginate, ethyl cellulose, hydroxyethyl cellulose, raffinose, stachyose, xanthan gum, glucosamine, and galactosamine. Preferably, the saccharide is a maltose-type disaccharide. The maltose-type disaccharide includes maltose, cellobiose, lactose, and the like. More preferably, the saccharide is maltose.

In the present invention, the saccharide content in the composition for the cryopreservation of cells is not particularly limited; however, the final saccharide concentration is preferably 0.01-10.0% by weight, more preferably 0.1-1.0% by weight. A final saccharide concentration within the abovementioned range is advantageous to exhibit a sufficient cryoprotective effect.

According to a preferred embodiment of the present invention, the composition for the cryopreservation of cells according to the present invention at least comprises sericin, amino acids and saccharides. The mixing ratio (by weight) of these components, sericin:amino acids:saccharides, in the composition for the cryopreservation of cells is typically 1:0.01-10.0:0.01-10.0, more preferably 1:0.1-1.0:0.1-1.0, and most preferably 1:0.4-0.8:0.3-0.7.

Other Cellular Cryoprotective Components

The composition for the cryopreservation of cells according to the present invention can further comprise other cellular cryoprotective components. The other cellular cryoprotective components are, for example, selected from the group consisting of dimethyl sulfoxide (DMSO), ethylene glycol, propylene glycol, and glycerol. They can be used in combination of two or more.

The content of the other cellular cryoprotective components in the composition for the cryopreservation of cells according to the present invention can be appropriately changed depending on the kind of components to be used; however, the final concentration of the components is preferably 1.0-40.0% by weight, more preferably 5.0-20.0% by weight. A final concentration of the other cellular cryoprotective components of 1.0% or more by weight is advantageous to exhibit a sufficient cryoprotective effect, and a final concentration of less than 40.0% by weight is preferable to reduce cytotoxicity.

When the other cellular cryoprotective component is dimethyl sulfoxide, the dimethyl sulfoxide content of the composition for the cryopreservation of cells is preferably 5.0-15.0% by weight. When the other cellular cryoprotective component is glycerol, the glycerol content of the composition for the cryopreservation of cells is preferably 5.0-20.0% by weight. From the viewpoint of the cellular cryoprotective effect, dimethyl sulfoxide is more desirable than glycerol.

Buffers

The composition for the cryopreservation of cells according to the present invention can further comprise a buffer. In the case where the composition for the cryopreservation of cells is in a solution form, i.e., a cryopreservation fluid, the pH range of the preservation fluid at a room temperature (for example, at 25° C.) is desirably selected to be 6.0-8.5, preferably 7.0-7.5. The pH range within the abovementioned range is advantageous to reduce effects on cell growth.

In the present invention, the buffer can be any kind as long as it meets the abovementioned pH conditions. Specific examples of the buffer include phosphoric acid buffers (for example, PBS), BES, TES, acetamidoglycine, glycine amides, glycylglycine, TRICINE, tris-ethanolamine, veronal, and HEPES. The buffer is preferably selected from the group consisting of PBS, TRICINE, and HEPES, and more preferably HEPES.

In the case where the composition for the cryopreservation of cells is in a solution form, i.e., a cryopreservation fluid, the concentration of the buffer to be contained therein is preferably 1-1000 mM, more preferably 1-200 mM, further preferably 5-200 mM, and furthermore preferably 5-50 mM. The concentration of the buffer within the abovementioned range can provide a buffering effect in the cryopreservation fluid and can reduce effects on cells.

Other Optional Components

The composition for the cryopreservation of cells according to the present invention can further comprise other optional components.

Examples of other optional components herein include additional components such as peptides, other proteins, sugar alcohols, amino saccharides, glycoproteins, and alcohols, pH controlling agents, moisturizing agents, preservatives, and viscosity controlling agents. They can be used in combination of two or more. The kind and the amount for use of the other optional components can be appropriately selected taking the kind of cells to be cryopreserved, the method of freezing, the period of freezing, and the like into consideration.

It is desirable that the composition for the cryopreservation of cells according to the present invention substantially does not contain the usual culture fluids or components derived from serum; however, if necessary, use of all or a part of them is not necessarily denied.

According to a preferred embodiment of the present invention, the composition for the cryopreservation of cells comprises components (a) to (d) in the amounts as follows:

(a) 0.01 to 10.0% by weight of sericin;
(b) 0.01 to 10.0% by weight of one or more components selected from the group consisting of amino acids and saccharides;
(c) 1.0 to 40.0% by weight of an additional cellular cryoprotective component selected from the group consisting of dimethyl sulfoxide, ethylene glycol, propylene glycol, and glycerol; and
(d) 1 to 1000 mM of a buffer.

According to a more preferred embodiment of the present invention, the composition for the cryopreservation of cells comprises components (a) to (d) in the amounts as follows:

(a) 0.01 to 10.0% by weight of sericin;
(b1) 0.01 to 10.0% by weight of amino acids;
(b2) 0.01 to 10.0% by weight of saccharides;
(c) 1.0 to 40.0% by weight of an additional cellular cryoprotective component selected from the group consisting of dimethyl sulfoxide, ethylene glycol, propylene glycol, and glycerol; and
(d) 1 to 1000 mM of a buffer.

The composition for the cryopreservation of cells according to the present invention can be obtained in a solid form by mixing the abovementioned components as they are, or if necessary, as an aqueous solution by dissolving the components in water.

Cryopreservation of Cells

The composition for the cryopreservation of cells according to the present invention is used in treating cells for cryopreservation. Namely, when cells are treated for cryopreservation, target cells are suspended in the composition according to the present invention in a liquid state and the resulting suspension is frozen by maintaining it under conditions for cryopreservation. When the cells are needed, the frozen cells and the composition according to the present invention are subjected to a thawing process, after which the cells can be recovered.

Therefore, according to the present invention, there is provided a method of cryopreserving cells comprising the steps of placing target cells in the composition for the cryopreservation of cells according to the present invention and cryopreserving them.

Here, upon placing the target cells in the composition for the cryopreservation of cells, the concentration of the cells is desirably 10,000-10,000,000 cells/ml.

In the present invention, a method for cryopreserving cells is not particularly limited. For example, target cells are suspended in the composition for the cryopreservation of cells according to the present invention in a state of solution, the suspension thus prepared is dispensed into freezing tubes, and the resulting tubes are placed directly in an ultra-low temperature freezer at −80° C. to freeze the cells. Alternatively, the freezing tubes can be placed in a programmed freezer to slowly freeze the cells. The preservation of the frozen cells can be carried out by maintaining the cells at the temperature used for freezing (for example, −80° C.).

Further, a method for thawing the cells is also not particularly limited; for example, the cells can be thawed by placing the cryopreserved freezing tubes in a water bath at 37° C.

According to another embodiment of the present invention, there is provided use of combination of sericin with one or more components selected from the group consisting of amino acids and saccharides in order to increase the survival rate of cells in cellular cryopreservation. Here, it is preferable that the combination of the components at least comprises sericin, amino acids, and saccharides.

EXAMPLES

The following examples will specifically explain the present invention; however, they are not to be construed to limit the scope of the invention.

Preparation of Sericin

Silk thread produced by domestic silkworms (*Bombyx mori*) was thoroughly washed, after which 100 g of the silk thread was heat-treated for hydrolysis at 96° C. for 2 hours in 2 L of 0.2% sodium acid carbonate aqueous solution as an extraction solvent to extract a sericin hydrolysate. The sericin hydrolysate extract thus obtained was filtered using a filter having an average pore size of 0.2 μm to remove coagulates, after which the resultant filtrate was desalted using a reverse osmosis membrane to obtain a colorless transparent sericin aqueous solution at a concentration of 0.2%.

Next, this aqueous solution was concentrated using an evaporator to a sericin concentration of about 2% and then subjected to lyophilization to obtain sericin in powder form at a purity of more than 90% and having an average molecular weight of about 30,000.

The average molecular weight of the sericin thus obtained was measured by the gel filtration chromatography method (using LC-9A (Shimadzu) as a measuring device and Superdex 75HR 10/30 (Pharmacia) as a column).

A sericin powder was obtained in the same manner as described above, except that the extraction solvent used for the extraction of sericin from silk thread was distilled water. In this case, the average molecular weight of the resulting sericin was about 100,000.

A sericin powder was obtained in the same manner as described above, except that the extraction solvent used for the extraction of sericin from silk thread was a 0.5% sodium acid carbonate aqueous solution. In this case, the average molecular weight of the resulting sericin was about 10,000.

The relationship between the kind of extraction solvent and the average molecular weight of the resulting sericin is shown in Table 1.

TABLE 1

| Average molecular weight of sericin | Extraction solvent |
|---|---|
| 100,000 | Distilled water |
| 30,000 | 0.2% sodium acid carbonate aqueous solution |
| 10,000 | 0.5% sodium acid carbonate aqueous solution |

Example 1

Study on Components—a (Saccharides)

Preparation of Composition for the Cryopreservation of Cells

Each composition for the cryopreservation of cells in a solution form (hereinafter referred to as "cryopreservation fluid" or occasionally referred to simply as "preservation fluid") was prepared according to the composition shown in Table 2 below and each designated as cryopreservation fluid a1 to a9.

Sericin used here was the sericin obtained above which has a molecular weight of 30,000.

As a buffer, PBS (phosphoric acid concentration: 9.5 mM) was used.

As a serum component, fetal bovine serum (hereinafter referred to as FBS) (GIBCO) was used.

TABLE 2

| Preservation fluid | Saccharides | | Sericin | PBS | FBS | DMSO |
|---|---|---|---|---|---|---|
| | Kind | Amount | | | | |
| a1 | — | — | — | — | 90.0 | 10.0 |
| a2 | — | — | 1.0 | 90.0 | — | 10.0 |
| a3 | Sucrose | 0.5 | 1.0 | 90.0 | — | 10.0 |
| a4 | Maltose | 0.5 | 1.0 | 90.0 | — | 10.0 |
| a5 | Trehalose | 0.5 | 1.0 | 90.0 | — | 10.0 |
| a6 | Maltitol | 0.5 | 1.0 | 90.0 | — | 10.0 |
| a7 | Dextran | 0.5 | 1.0 | 90.0 | — | 10.0 |
| a8 | Methylcellulose | 0.5 | 1.0 | 90.0 | — | 10.0 |
| a9 | — | — | — | 90.0 | — | 10.0 |

(Unit: g)

Cryopreservation Test

In the test, mouse myeloma P3U1 cells (obtained from Japan Health Sciences Foundation) cultured using an RPMI1640 medium (Asahi Techno Glass) containing 10.0% FBS were used.

The cells were suspended at a concentration of about $1.0 \times 10^6$ cells/ml in individual cryopreservation fluids and the individual suspensions were dispensed in a volume of 1 ml into freezing tubes (Asahi Techno Glass). Next, the tubes were cryopreserved using a freezer at −80° C. for 30 days, after which the tubes were soaked in a water bath at 37° C. for thawing.

The viable cell density in the thawed preservation fluids was calculated using a trypan blue dye exclusion method to obtain the survival rate of the cells in each cryopreservation fluid.

Results are shown in Table 3.

Preservation fluid a4 supplemented with maltose exhibited an excellent cryoprotective effect as compared to the preservation fluid supplemented with sericin alone (preservation fluid a2) and other preservation fluids supplemented with saccharides.

TABLE 3

| Preservation fluid | Survival rate (%) | |
|---|---|---|
| | Average | Standard deviation |
| a1 | 75.2 | 4.7 |
| a2 | 53.5 | 3.8 |
| a3 | 57.5 | 4.2 |
| a4 | 67.3 | 3.7 |
| a5 | 60.1 | 3.2 |
| a6 | 58.4 | 3.8 |
| a7 | 60.3 | 5.2 |
| a8 | 62.7 | 3.3 |
| a9 | 28.8 | 2.8 |

(N = 3)

Example 2

Study on Components—b (Amino Acids)

Cryopreservation fluids b1 to b9 were prepared in the same manner as in Example 1, except that each composition was as shown in Table 4 below.

TABLE 4

| Preservation fluid | Amino acids | | Sericin | Maltose | PBS | FBS | DMSO |
|---|---|---|---|---|---|---|---|
| | Kind | Amount | | | | | |
| b1 | — | — | — | — | — | 90.0 | 10.0 |
| b2 | — | — | 1.0 | 0.5 | 90.0 | — | 10.0 |
| b3 | Serine | 0.3 | 1.0 | 0.5 | 90.0 | — | 10.0 |
| b4 | Threonine | 0.3 | 1.0 | 0.5 | 90.0 | — | 10.0 |
| b5 | Proline | 0.3 | 1.0 | 0.5 | 90.0 | — | 10.0 |
| b6 | Glutamine | 0.3 | 1.0 | 0.5 | 90.0 | — | 10.0 |
| b7 | Proline + Glutamine | 0.3 each | 1.0 | 0.5 | 90.0 | — | 10.0 |
| b8 | Proline + glutamine | 0.3 each | 1.0 | — | 90.0 | — | 10.0 |
| b9 | — | — | — | — | 90.0 | — | 10.0 |

(Unit: g)

The cryopreservation test was also carried out in the same manner as in Example 1, except that preservation fluids b1 to b9 were used as cryopreservation fluids.

Results are shown in Table 5.

Preservation fluid b7 supplemented with 0.3% each of proline and glutamine exhibited an excellent cryoprotective effect as compared to the preservation fluids supplemented with sericin alone or with a single amino acid. Further, preservation fluid b7 exhibited about the same cryoprotective effect as the fluid with the use of serum (preservation fluid b1).

TABLE 5

| Preservation fluid | Survival rate (%) | |
|---|---|---|
| | Average | Standard deviation |
| b1 | 76.5 | 2.8 |
| b2 | 66.8 | 4.3 |
| b3 | 70.2 | 4.1 |
| b4 | 67.7 | 3.8 |
| b5 | 72.1 | 5.5 |
| b6 | 72.6 | 5.7 |
| b7 | 79.3 | 3.1 |
| b8 | 64.8 | 4.2 |
| b9 | 28.8 | 2.6 |

(N = 3)

Example 3

Study on Components—c (Other Cellular Cryoprotective Components)

Cryopreservation fluids c1 to c6 were prepared in the same manner as in Example 1, except that each composition was as shown in Table 6 below.

TABLE 6

| Preservation fluid | Other cellular cryoprotective comp. | | Sericin | PBS | FBS | Maltose | Proline | Glutamine |
|---|---|---|---|---|---|---|---|---|
| | Kind | Amount | | | | | | |
| c1 | Dimethyl sulfoxide | 10.0 | — | — | 90.0 | — | — | — |
| c2 | Dimethyl sulfoxide | 10.0 | 1.0 | 90.0 | — | 0.5 | 0.3 | 0.3 |
| c3 | Ethylene glycol | 10.0 | 1.0 | 90.0 | — | 0.5 | 0.3 | 0.3 |
| c4 | Propylene glycol | 10.0 | 1.0 | 90.0 | — | 0.5 | 0.3 | 0.3 |
| c5 | Glycerol | 10.0 | 1.0 | 90.0 | — | 0.5 | 0.3 | 0.3 |
| c6 | — | — | 1.0 | 100 | — | 0.5 | 0.3 | 0.3 |

(Unit: g)

The cryopreservation test was also carried out in the same manner as in Example 1, except that preservation fluids c1 to c6 were used as cryopreservation fluids.

Results are shown in Table 7.

All of the preservation fluids respectively supplemented with dimethyl sulfoxide, ethylene glycol, propylene glycol, and glycerol (preservation fluids c2 to c5) exhibited an excellent cryoprotective effect.

TABLE 7

| Preservation fluid | Survival rate (%) Average | Standard deviation |
|---|---|---|
| c1 | 75.2 | 3.4 |
| c2 | 77.3 | 4.1 |
| c3 | 70.1 | 2.2 |
| c4 | 67.2 | 2.5 |
| c5 | 73.8 | 2.1 |
| c6 | 52.3 | 2.8 |

(N = 3)

Example 4

Study on Components—d (Buffers)

Cryopreservation fluids d1 to d6 were prepared in the same manner as in Example 1, except that each composition was as shown in Table 8 below.

TABLE 8

| Preservation fluid | Buffer Type | Conc. (mM) | Sericin | Maltose | Proline | Glutamine | FBS | DMSO |
|---|---|---|---|---|---|---|---|---|
| d1 | — | — | — | — | — | — | 90.0 | 10.0 |
| d2 | PBS | 100 | 1.0 | 0.5 | 0.3 | 0.3 | — | 10.0 |
| d3 | TRICINE | 100 | 1.0 | 0.5 | 0.3 | 0.3 | — | 10.0 |
| d4 | HEPES | 100 | 1.0 | 0.5 | 0.3 | 0.3 | — | 10.0 |
| d5 | HEPES | 200 | 1.0 | 0.5 | 0.3 | 0.3 | — | 10.0 |
| d6 | HEPES | 50 | 1.0 | 0.5 | 0.3 | 0.3 | — | 10.0 |

(Unit: g)

The cryopreservation test was also carried out in the same manner as in Example 1, except that preservation fluids d1 to d6 were used as cryopreservation fluids.

Results are shown in Table 9.

All of the preservation fluids respectively supplemented with PBS, HEPES, and TRICINE (d2 to d6) exhibited an excellent cryoprotective effect. Further, the cryoprotective effect was excellent with the buffer at all measured concentrations (d4 to d6).

TABLE 9

| Preservation fluid | Survival rate (%) Average | Standard deviation |
|---|---|---|
| d1 | 77.4 | 2.8 |
| d2 | 78.6 | 4.2 |
| d3 | 72.5 | 2.8 |
| d4 | 74.5 | 3.1 |
| d5 | 80.4 | 2.2 |
| d6 | 70.3 | 4.4 |

(N = 3)

Example 5

Study on Components—e (Average Molecular Weight of Sericin)

Cryopreservation fluids e1 to e6 were prepared in the same manner as in Example 1, except that and each composition was as shown in Table 10 below in which sericin preparations having different average molecular weights were used.

In this example, the sericin preparations obtained in the abovementioned section "Preparation of sericin," each having an average molecular weight of about 10,000, about 30,000, and about 100,000, were used.

TABLE 10

| Preservation fluid | Sericin (average molecular weight) 10,000 | 30,000 | 100,000 | Maltose | Proline | Glutamine | PBS | FBS | DMSO |
|---|---|---|---|---|---|---|---|---|---|
| e1 | — | — | — | — | — | — | — | 90.0 | 10.0 |
| e2 | 1.0 | — | — | 0.5 | 0.3 | 0.3 | 90.0 | — | 10.0 |
| e3 | — | 1.0 | — | 0.5 | 0.3 | 0.3 | 90.0 | — | 10.0 |
| e4 | — | — | 1.0 | 0.5 | 0.3 | 0.3 | 90.0 | — | 10.0 |
| e5 | — | — | — | 0.5 | 0.3 | 0.3 | 90.0 | — | 10.0 |
| e6 | — | — | — | — | — | — | 90.0 | — | 10.0 |

(Unit: g)

The cryopreservation test was also carried out in the same manner as in Example 1, except that preservation fluids e1 to e6 were used as cryopreservation fluids.

Results are shown in Table 11.

The cryopreservation fluid supplemented with sericin having an average molecular weight of 30,000 (preservation fluid e3) exhibited an excellent cryoprotective effect as compared to the preservation fluids supplemented with sericin having a higher or lower molecular weight.

TABLE 11

| Preservation fluid | Survival rate (%) | |
|---|---|---|
| | Average | Standard deviation |
| e1 | 72.4 | 6.6 |
| e2 | 54.7 | 5.1 |
| e3 | 74.9 | 3.3 |
| e4 | 50.7 | 4.4 |
| e5 | 47.8 | 3.8 |
| e6 | 24.2 | 4.0 |

Example 6

Cryopreservability of Other Kinds of Cells

The cryopreservation test was carried out in the same manner as in Example 1, except that the cells to be used were replaced with other kinds of cells and cryopreservation fluids e1, e3, and e6 in Example 5 were used as cryopreservation fluids.

Other kinds of cells used here were normal human dermal fibroblast (NHDF) cells (obtained from Bio Whittaker), rat adrenal medulla pheochromocytoma cells (PC-12) (obtained from Japan Health Sciences Foundation), *Spodopera frugiperda*-derived insect cells (Sf-9) (obtained from GIBCO), CHO (Chinese hamster ovary) cells (obtained from Riken), HepG2 cells (obtained from Riken), hybridoma cells (Cytotechnology 10, 15-23, 1992), human epidermal keratinocyte cells (HEK) (obtained from Cell Applications, Inc.), and rabbit cornea cells (RC4) (obtained from Riken). NHDF cells are used for treatment of wounds, study of cytotoxicity, and like. Hybridoma cells produce monoclonal antibodies, CHO cells and Sf-9 cells are transformed by genetic engineering technology and produce physiologically active substances and thus these cells are industrially used as a means for the production of proteins. Further, HepG2 cells are useful as an artificial liver model and PC-12 cells are useful as a material to study a process of differentiation into nerve cells. HEK cells are used in a skin irritation test, and RC4 cells are used for an eye toxicity test for cosmetics, agricultural chemicals, and the like.

Regarding hybridoma cells, the survival rate was measured after a re-freezing/thawing process after a normal freezing/thawing process.

Results are shown in Table 12.

The cryopreservation fluid according to the present invention (preservation fluid e3) exhibited a survival rate about the same as that with the use of serum (preservation fluid e1) in individual cells derived from different sources.

TABLE 12

| Kind of cells | Survival rate (%) Preservation fluid | | |
|---|---|---|---|
| | e1 | e3 | e6 |
| NHDF | 38.0 | 39.3 | 5.3 |
| PC-12 | 89.4 | 88.5 | 78.2 |
| Sf-9 | 44.3 | 42.1 | 10.1 |
| CHO | 71.2 | 67.3 | 31.1 |
| HepG2 | 58.5 | 56.8 | 14.8 |
| Mouse hybridoma (Frozen twice) | 66.7 | 79.5 | 28.4 |
| HEK | 94.7 | 97.0 | 63.2 |
| RC4 | 92.3 | 90.5 | 51.2 |

(N = 3)

The invention claimed is:

1. A composition for the cryopreservation of cells, at least comprising sericin, proline, glutamine and maltose, wherein the final concentrations of sericin and maltose are each 0.01 to 10.0% by weight and the final concentration of proline and glutamine is 0.01 to 10.0% by weight.

2. The composition for the cryopreservation of cells according to claim 1, wherein the average molecular weight of sericin ranges from 10,000 to 100,000.

3. The composition for the cryopreservation of cells according to claim 1, which further comprises at least one additional cellular cryoprotective component selected from the group consisting of dimethyl sulfoxide, ethylene glycol, propylene glycol, and glycerol.

4. The composition for the cryopreservation of cells according to claim 1, which is an aqueous solution.

5. The composition for the cryopreservation of cells according to claim 1, which further comprises a buffer so that the pH of said composition in a solution ranges from 6.0 to 8.5 at room temperature.

6. The composition for the cryopreservation of cells according to claim 1, which comprises components (a) to (d) in the amounts as follows:
   (a) 0.01 to 10.0% by weight of sericin;
   (b1) 0.01 to 10.0% by weight of proline and glutamine;
   (b2) 0.01 to 10.0% by weight of maltose;
   (c) 1.0 to 40.0% by weight of an additional cellular cryoprotective component selected from the group consisting of dimethyl sulfoxide, ethylene glycol, propylene glycol, and glycerol; and
   (d) 1 to 1000 mM of a buffer.

7. A method for the cryopreservation of cells, which comprises the steps of placing target cells in the composition for the cryopreservation of cells of claim 1 and cryopreserving the cells.

8. A method of preparing a composition to increase the survival rate of cells in cellular cryopreservation, comprising combining sericin, proline, glutamine and maltose, wherein the final concentrations of sericin, and maltose are each 0.01 to 10.0% by weight and the final concentration of proline and glutamine is 0.01 to 10.0% by weight.

* * * * *